United States Patent [19]
Riddle et al.

[11] Patent Number: 5,741,233
[45] Date of Patent: Apr. 21, 1998

[54] INTRODUCER DEVICE AND METHODS OF USE THEREOF

[75] Inventors: Richard S. Riddle, Keene, N.H.; Matthew Muraski, Maple Grove, Minn.; Jerome W. Frederick, III, Rindge; Jonathan A. LeClair, Keene, both of N.H.

[73] Assignee: TFX Medical, Incorporated, Jaffrey, N.H.

[21] Appl. No.: 545,999

[22] Filed: Oct. 20, 1995

[51] Int. Cl.$^6$ .................................. A61M 5/178
[52] U.S. Cl. .................... 604/165; 604/164; 604/160
[58] Field of Search ........................ 604/158, 160, 604/164, 165, 167, 280

[56] References Cited

U.S. PATENT DOCUMENTS

| | | | |
|---|---|---|---|
| 862,712 | 8/1907 | Collins. | |
| 3,860,006 | 1/1975 | Patel | 128/347 |
| 4,168,709 | 9/1979 | Bentov | 128/345 |
| 4,243,050 | 1/1981 | Littleford | 128/784 |
| 4,596,559 | 6/1986 | Fleischhacker | 604/170 |
| 4,772,266 | 9/1988 | Groshong. | |
| 4,793,363 | 12/1988 | Ausherman et al. | 128/754 |
| 4,834,708 | 5/1989 | Pillari | 604/165 |
| 5,064,414 | 11/1991 | Revane | 604/168 |
| 5,098,392 | 3/1992 | Fleischhacker et al. | 604/165 |
| 5,141,497 | 8/1992 | Erskine | 604/165 |
| 5,147,336 | 9/1992 | Wendell et al. | 604/283 |
| 5,163,903 | 11/1992 | Crittenden et al. | 604/96 |
| 5,167,634 | 12/1992 | Corrigan, Jr. et al. | 604/160 |
| 5,221,263 | 6/1993 | Sinko et al. | 604/161 |
| 5,250,033 | 10/1993 | Evans et al. | 604/160 |
| 5,334,157 | 8/1994 | Klein et al. | 604/160 |
| 5,380,293 | 1/1995 | Grant | 604/177 |
| 5,391,152 | 2/1995 | Patterson | 604/165 |

FOREIGN PATENT DOCUMENTS

WO 93/13822  7/1993  WIPO.

OTHER PUBLICATIONS

TFX Medical product literature for T-Peel™ Peelable Introducers.
Quinton Instrument Co. literature.
B. Baun Medical Inc. literature.

*Primary Examiner*—Sam Rimell
*Attorney, Agent, or Firm*—David G. Conlin; Peter F. Corless

[57] ABSTRACT

The present invention comprises an improved medical introducer device that comprises a releasably locking dilator and circumscribing sheath as well as a tactile indicator to conveniently inform a user of the device whether the dilator/sheath assembly is in a locked or unlocked position. In preferred aspects, the introducer device also includes a visual indicator to provide visual indication to a device user that the dilator and sheath are either in a locked or unlocked position, and a lead-in section at the sheath proximal end to facilitate insertion of a dilator, guide wire, catheter, etc. through the device.

23 Claims, 2 Drawing Sheets

INTRODUCER DEVICE AND METHODS OF USE THEREOF

BACKGROUND OF THE INVENTION

1. Field of the Invention

The present invention relates to a dilator/sheath introducer device for insertion of a catheter, guide wire and the like into a patient. More particularly, in a preferred aspect the invention provides an improved introducer device that comprises a releasably locking dilator and circumscribing sheath as well as a tactile indicator to conveniently inform a user of the device whether the dilator/sheath assembly is in a locked or unlocked position.

2. Background

Dilator/sheath introducer devices have been employed for inserting catheters, guide wires and the like into patients. A typical procedure provides for insertion of a dilator or needle within a splittable sheath into the vasculature of a patient. After insertion, the dilator may be removed leaving the sheath protruding from the patient's vein. A diagnostic or therapeutic catheter (e.g. a central venous access catheter) or guide wire or other object such as a capsule, is then inserted through the sheath into the patient. The encasing sheath is then typically longitudinally sheared and removed from the catheter or guide wire and the patient such as by applying opposing force to opposed wings or tabs of the introducer device. See U.S. Pat. Nos. 5,334,157; 5,221,263; 5,141,497; 5,098,392; 4,772,266; and 4,243,050.

It is possible during manipulation and initial insertion of the introducer device for the dilator and sheath to become separated. Accordingly, preferably the dilator locks to the circumscribing sheath to avoid undesired axial movement of the dilator with respect to the sheath such as may occur during initial insertion of the dilator into a patient.

The locking mechanism should be relatively easy to operate so the dilator can be readily removed from the sheath at an appropriate time during a medical procedure, e.g., when a catheter or guide wire is to be inserted through the sheath. However, prior devices with releasably locking dilator/sheath components may prove difficult to disengage during use, or it may be difficult to determine whether the sheath and dilator components are in a locked or unlocked position. For example, the device reported in U.S. Pat. No. 4,243,050 to Littleford can entail relatively careful visual inspection to determine if sheath and dilator components are in a locked or unlocked position. Such a visual inspection may be highly inconvenient, particularly during a medical procedure.

It thus would be desirable to have an introducer device that comprises a releasable lock to avoid undesired movement of the dilator/sheath assembly. It would be further desirable to have such an introducer device where medical personnel could readily lock and unlock the dilator/sheath assembly. It would be particularly desirable to have such an introducer device where it could be readily determined whether the dilator and sheath components are in locked or unlocked positions.

SUMMARY OF THE INVENTION

The present invention comprises an improved dilator/sheath introducer device that comprises a releasable lock to avoid undesired movement of the dilator with respect to the sheath and further comprises a tactile indicator to conveniently inform a user of the device whether the dilator/sheath assembly is in a locked or unlocked position.

Preferably, the tactile indicator comprises a positive stop or inhibitor which provides the device user tactile indication of whether the assembly of the dilator with circumscribing sheath is releasably secured (locked) so that axial movement of the dilator within the circumscribing sheath is avoided, or whether the dilator/sheath assembly is disengaged (unlocked) so that the dilator may be removed from the sheath, e.g. after the sheath has been inserted into a patient's vein. As used herein, the terms "locked", "secured" and the like with regard to the dilator/sheath assembly indicate that axial withdrawal of the dilator out of the sheath is substantially prevented during regular use of the device.

In a preferred embodiment, the positive stop comprises a plurality of mating surfaces on the proximal ends of the dilator and sheath wherein the surfaces mate to indicate to a device user that the dilator/sheath assembly is locked or unlocked. Such mating surfaces are suitably of a variety of configurations so long as the desired tactile indication is provided. Preferably the surfaces mate to inhibit or prevent further rotation of the dilator or sheath and to thereby indicate the assembly is in a locked or unlocked position.

In one particularly preferred configuration, the positive stop comprises a flange on the dilator proximal end that mates (upon axial rotation of the dilator and/or sheath components) with a flange on the sheath proximal end to provide tactile indication that the dilator and sheath are either in a locked or unlocked position. The dilator and sheath components then can be moved to a locked or unlocked position therefrom by such axial rotation in the opposite direction. Preferably, mating of the dilator and sheath flanges indicates the dilator and sheath components are in an unlocked position. The releasable dilator/sheath locking mechanism suitably may comprise such sheath and dilator flanges which provide the tactile indication.

In a further aspect, the introducer device of the invention includes a visual indicator to provide visual indication to a device user that the dilator/sheath assembly is in a locked or unlocked position. The visual indicator is suitably outwardly extending flanges, preferably positioned on the dilator proximal end. For example, the visual indicator is suitably opposing protrusions on the dilator, preferably extending from the dilator hub on the dilator proximal end. It is also preferred that such visual indicators are configured to aid handling and manipulation of the introducer device.

In another aspect, the introducer device of the invention includes a lead-in section at the sheath proximal end adapted to facilitate insertion of a dilator, guide wire, catheter or the like into the sheath. The lead-in section is preferably downwardly tapered toward the sheath distal end, such as being conically or funnel shaped.

The invention also includes methods for inserting a catheter, guide wire or the like into a patient comprising inserting the introducer device into a patient and inserting a catheter, guide wire or the like through the device into the patient.

Other aspects of the invention are disclosed infra.

DETAILED DESCRIPTION OF THE INVENTION

The sheath component of an introducer device of the invention has a bore adapted to snugly receive a dilator for insertion into a vein or artery of a patient while circumscribed by the sheath. The dilator component is adapted to be inserted within the sheath and preferably is also bored. Typically, the sheath component is splittable, i.e. the sheath may be axially sheared such as along diametrically opposed longitudinal score lines as desired. Additionally, the sheath component preferably will comprise a hub portion at the sheath proximal end to facilitate such shearing. (In accordance with conventional practice, "proximal end" designates herein the specified end closest to the medical personnel manipulating the introducer device, and "distal end" designates herein the specified end closest to the patient.) Preferably, the sheath hub contains a pair of opposing wings or tabs that can facilitate axial shearing of the sheath.

Figure 1:
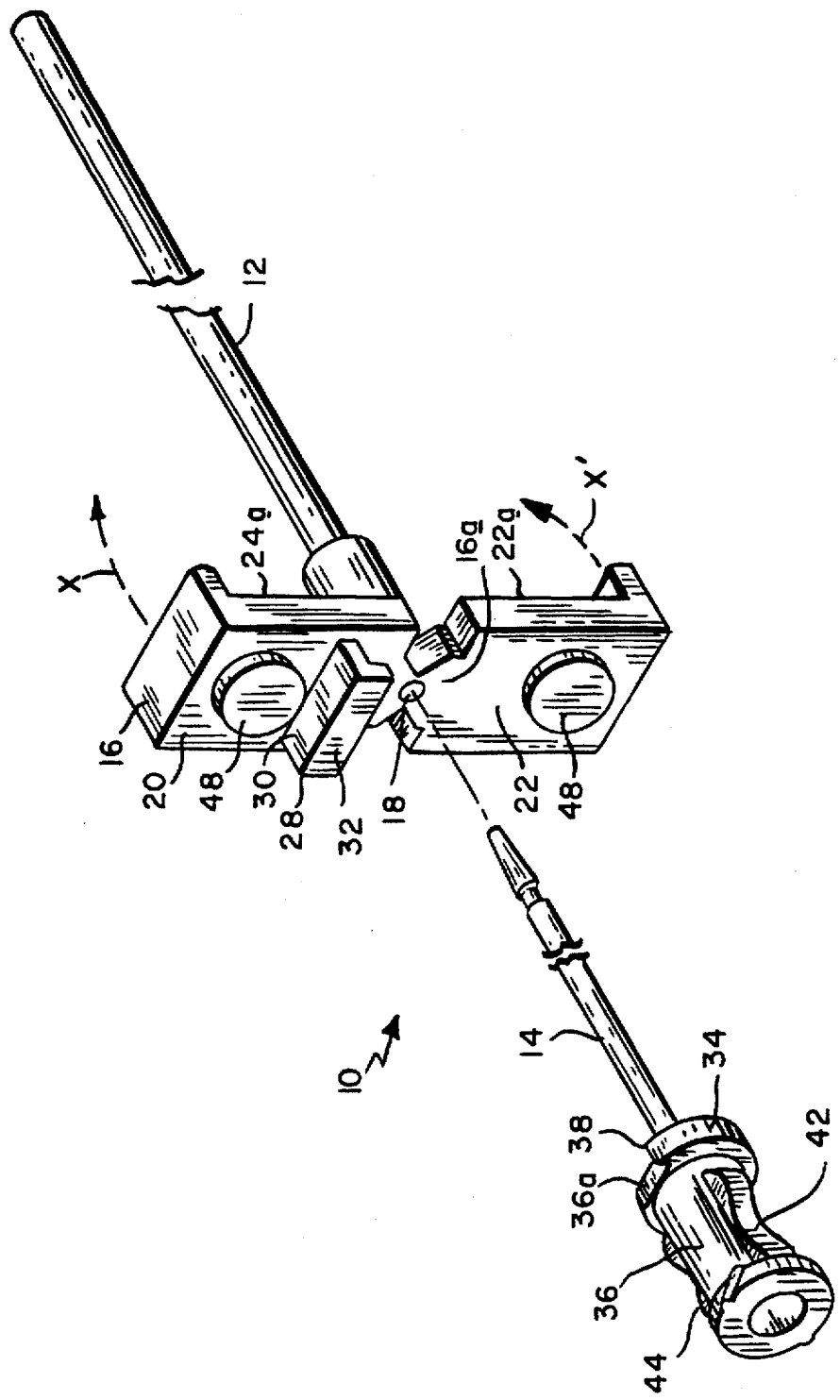
FIG. 1 shows an above view of separated splittable sheath and dilator components of an introducer device of the invention.
Figure 2:
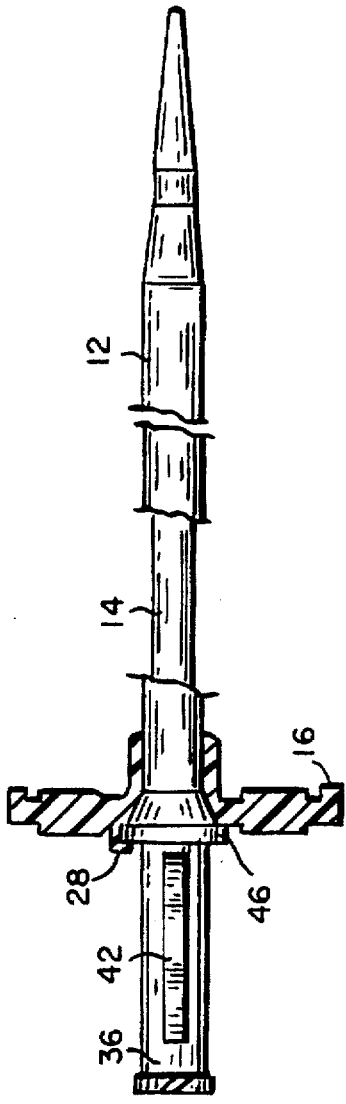
FIG. 2 shows a partial cut-away side view of an introducer device of the invention where the dilator is circumscribed by the sheath component.
Figure 3:
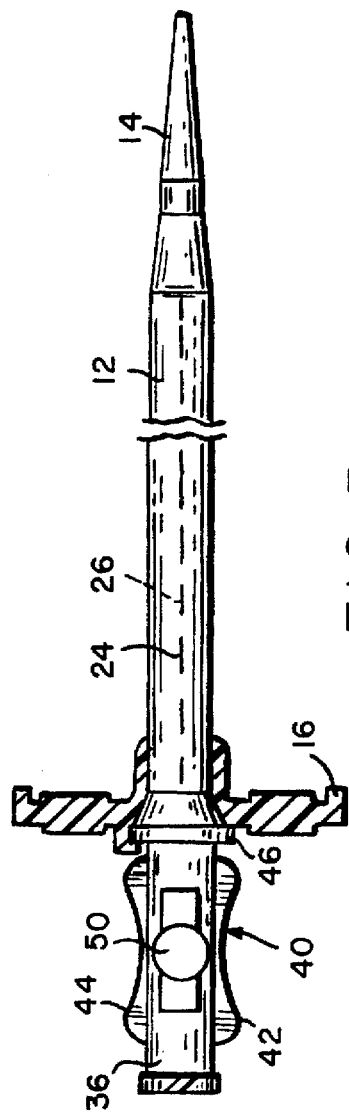
FIG. 3 shows an above view of an introducer device of the invention where the dilator is circumscribed by the sheath component.

Referring now to the Drawings, where particularly preferred introducer devices of the invention are depicted, FIGS. 1–3 show introducer device 10 that includes sheath 12 and dilator 14. Sheath 12 has sheath hub 16 at the sheath proximal end and bore 18 adapted to receive dilator 14. Sheath hub 16 preferably includes opposed wing or tab portions 20 and 22 to aid axial shearing of the sheath, specifically by directing pressure to wings 20 and 22 along directions x and x' as shown in FIG. 1. Preferably sheath 12 also includes axially extending, diametrically score lines 24 and 26 as shown in FIG. 3 to facilitate axial shearing upon engaging wings 20 and 22. Dilator component 14 is inserted into and is circumscribed by sheath 12 as clearly depicted in FIGS. 2 and 3 during use of device 10.

Sheath 12 and dilator 14 can be releasably locked when dilator 14 is fully inserted into sheath 12 as shown in FIGS. 2 and 3. A variety of locking mechanisms can be employed. A preferred assembly is shown in the Drawings where non-threaded mating surfaces integral to the dilator and sheath provide the releasable lock. More specifically, lock flange 28 comprising upstanding portion 30 with laterally extending flange 32 on sheath hub 16 is adapted to engage lip 34 on dilator hub 36. With dilator 14 inserted fully into sheath 12 (i.e. where dilator hub bottom face 36a mates with sheath hub top face 16a), the dilator and/or sheath can be rotated axially so that lip 34 is positioned under flange 32, thereby releasably locking the dilator/sheath assembly and preventing undesired axial movement of dilator 14. Other locking mechanisms also may be employed such as other non-threaded integral mating flange configurations; a threaded or luer lock system where the dilator and sheath are releasably locked through a threaded or luer lock engagement, e.g. where the distal end of the dilator hub screws into the proximal end of the sheath hub, although such a threaded system may be less convenient during use of the device; or a separate non-integral locking piece (or at least non-integral to at least one of the sheath and dilator components) such as a clip to releasably attach the sheath and dilator components, although such a non-integral locking device is generally less preferred because of the bulk of the non-integral component and if it entails an additional item that must be accounted for during a medical procedure.

As discussed above, device 10 also includes a tactile indicator to inform a device user whether the dilator/sheath assembly is in a locked or unlocked position without visual inspection of the device. Again, a variety of configurations can be employed so long as the device user is provided tactile indication of whether the dilator/sheath assembly is releasably locked so that axial movement of the dilator within the circumscribing sheath is avoided, or whether the dilator/sheath assembly is unlocked so that the dilator may be removed from the sheath.

A preferred indicator is a positive stop that comprises a plurality of mating surfaces on the proximal ends of the dilator and sheath wherein the surfaces mate to indicate to a device user that dilator/sheath assembly is locked or unlocked. Preferably at least one surface on the sheath mates with at least one surface on the dilator to provide tactile indication of locking or unlocking.

Figures 4A, 4B:
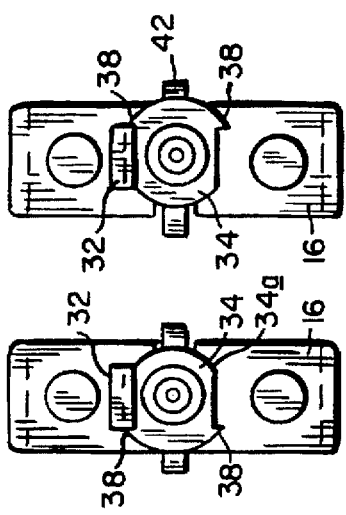
FIGS. 4A–4C show top views of a preferred introducer device of the invention with the dilator circumscribed by the sheath, and the dilator/sheath assembly are in unlocked positions (FIGS. 4A and 4B) and a locked position (FIG. 4C).
Figure 4C:
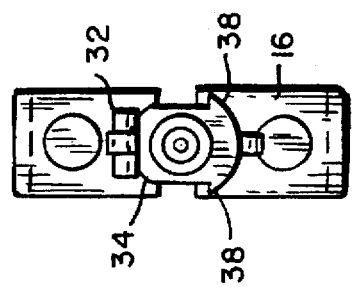

In one particularly preferred embodiment depicted in the Drawings, indicator flange 38 extends laterally outward from each side of dilator lip 34 and mates (upon axial rotation of the dilator and/or sheath components) with lock flange 28 (particularly portion 30 thereof) to provide tactile indication that the dilator and sheath are in an unlocked position. The dilator and sheath components then can be moved to a locked position therefrom by axial rotation in the opposite direction. Reference is made to FIGS. 4A and 4B which depict the dilator/sheath assembly in unlocked positions with indicator flange 38 abutting lock flange 28 so that further axial rotation against lock flange 28 is prevented thereby providing tactile indication to the device user that the dilator/sheath assembly is in an unlocked position. FIG. 4C shows the dilator/sheath assembly in a locked position, with lip 34 secured under flange 32, and wherein dilator 14 has been rotated about 90° from the unlocked positions depicted in FIGS. 4A and 4B.

Other tactile indicators also may be suitably employed in devices of the invention. For example, dilator lip 38 may contain a lateral flange extending perpendicular to flange 38 shown in FIGS. 4A–4C that would abut locking flange 28 to provide tactile indication that the dilator/sheath assembly is in a locked relationship. Such an additional indicator flange could be used in combination with flange 38 as shown so that tactile indication would be provided both upon locking and unlocking of the dilator/sheath assembly. Such an additional indicator flange may suitably extend from lip face 34a shown in FIG. 4A. Additionally, rather than abutting a locking flange, an indicator flange on the dilator hub may mate with a separate surface on the sheath not associated with the releasable dilator/sheath lock, although it is generally preferred that the tactile indicator is configured in combination with, i.e. is an integral part of, the releasable dilator/sheath lock. For example, one or more flanges could extend downwardly from the dilator hub (toward dilator distal end) and mate with the sheath hub, e.g. wing sidewalls 22a and/or 24a, when the dilator/sheath assembly is an unlocked position. The tactile indicator also may be a non-integral component of the introducer device, or non-integral to at least one of the sheath and dilator components, such as a clip that abuts the sheath when the dilator/sheath components are in an unlocked position, although again such a non-integral component may be less preferred because of bulk that may render use of the device less convenient and if it entails an additional item that must be accounted for during a medical procedure.

Device 10 also may include a visual indicator 40 to provide convenient visual indication to a device user that the dilator/sheath assembly is in a locked or unlocked position. A variety of indicators may be employed such as colored markers on the device, particularly on the dilator hub, or some type of protrusion on the dilator hub or other selected configuration on the dilator proximal end. One or more protrusions on the dilator proximal end is a generally preferred visual indicator.

In a preferred embodiment clearly depicted in FIGS. 1 and 3, visual indicator 40 suitably comprises opposing, outwardly extending protrusions or tabs 42 and 44 positioned on the dilator proximal end. During use of the device, alignment of tabs 42 and 44 indicate whether the dilator/sheath assembly is in a locked or unlocked position. Thus, for device 10 shown in the Drawings, alignment of tabs 42 and 44 along axis y (FIG. 3) of sheath wing portions 20 and 22 visually indicates the dilator/sheath assembly is in a locked position, and substantially perpendicular alignment of tabs 40 and 42 with respect to axis y (see FIG. 2) visually indicates the dilator/sheath assembly is in the unlocked position.

It is also preferred that such visual indicators are configured to aid a user's handling and manipulation of the introducer device. Thus, as shown in FIGS. 1 and 3, tabs 42 and 44 are shaped to form finger grips to facilitate handling of the device by medical personnel.

Device 10 preferably also includes lead-in section 46 at the sheath proximal end adapted to facilitate insertion of a dilator, guide wire, catheter or the like. Lead-in section 46 is preferably downwardly tapered toward the sheath distal end, such as being cortically or funnel shaped, as generally shown in FIGS. 2-3. Such a lead-in section may be suitably notched in alignment with score lines 24 and 26 to facilitate axial shearing of sheath 12.

Device 10 also may be supplied to a medical facility in a variety of sizes, including different lengths as well as different diameters of the sheath and dilator components as may be required for varying medical procedures. The respective sizes may be marked on the introducer devices in a variety of ways, including e.g. color-coded or numerical markers 48 positioned on the sheath hub or similar marker 50 on the dilator hub.

Sheath component 12 is preferably formed in an insert molding process as is known in the art wherein the sheath 12 is extruded and then the sheath hub 16 with wings 20 and 22 are molded directly thereon. It also would be possible to separately form the sheath hub and then adhere the hub onto the separately formed sheath such as by a suitable adhesive. Although generally less preferred, it is also possible to interpose a mounting unit such as a plastic strip between the sheath hub and the sheath. The components of device 10 can be formed from a number of materials as will be appreciated by those skilled in the art. For example, the sheath and sheath hub are suitably each formed from a polyethylene. Sheath 12 is preferably formed from other fluorinated resins, e.g. a fluorinated ethylene-propylene resin (FEP), and also could be formed from a tetrafluoroethylene polymer such as TEFLON. Dilator 14 and dilator hub 36 are preferably also made by such a insert molding process where the dilator is extruded and the dilator hub molded directly thereon. The dilator and dilator hub are also suitably formed from a polyethylene. The dilator is preferably formed from a fluorinated ethylene-propylene resin (FEP), and also could be formed from other fluorinated resins, e.g. a tetrafluoroethylene polymer such as TEFLON. In addition to polyethylene, both the sheath hub and dilator hub also may be suitably formed from a polypropylene, or be of the same composition as the sheath and dilator, respectively, e.g. FEP. For at least some applications, dilator 14 also may be formed from stainless steel or other metal with sharpened distal end.

Suitable dimensions of the components of an introducer device of the invention can suitably vary rather widely and can be readily determined by those skilled in the art based on the present disclosure. In general, sheath 12 and dilator 14 should have a diameter capable of being inserted into a selected vein of a patient, and sheath 12 should have a diameter sufficient to accommodate a catheter, guide wire or the like. Preferably the cross-sectional diameter of sheath 12 is between about 0.060 and 0.360 inches and may suitably be tapered from such diameter at its distal end as depicted in FIGS. 2 and 3. The cross-sectional diameter of dilator 16 suitably between about 0.050 and 0.350 inches and preferably is tapered from such diameter at its distal end as shown in FIGS. 1–3 to facilitate insertion of the dilator into a patient. Preferably the overall length of introducer device 10, represented as length 1 in FIG. 2, is between about 5.0 and 17.0 inches, with the length of sheath 12 (distance m in FIG. 2) being between about 3.0 and 16.0 inches, and the dilator extending from sheath distal end (length n in FIG. 2) between about 0.500 and 2.50 inches. Wings 20 and 22 preferably extend from sheath centerpoint to the wing end (distance t in FIG. 2) between about 0.500 and 1.00 inches. Again, dimensions outside these ranges also will be suitable for various applications.

A particularly preferred introducer device of the invention is of the configuration shown in the Drawings, wherein the overall length of introducer device 10 (length I) is 7.5 inches; the length of sheath 12 (length m) is 6.0 inches; dilator 14 extends from sheath distal end (length n) 1.5 inches; the length of dilator 14 with hub thereon is 8.5 inches; and wings 20 and 22 extend from sheath centerpoint (distance t in FIG. 2) 0.600 inches.

An introducer device of the invention may be suitably used as follows for placement of a catheter, guide wire, capsule, etc. in a patient.

The introducer device 10 is inserted into a patient via dilator 14 wherein lip 34 is positioned under flange 32 to releasably lock the dilator/sheath assembly and prevent the dilator extending upwardly out of sheath 12.

After sheath 12 has been positioned as desired in the patient, the dilator can be removed from the sheath. The dilator/sheath assembly can be unlocked by relative rotation of dilator with respect to the sheath so that lip 34 is not positioned under flange 32 such as shown in FIGS. 4A and 4B. The medical personnel can conveniently determine that the dilator/sheath assembly is in an unlocked position by rotating the dilator until tactile indication of unlocking is provided in accordance with the invention, e.g. as shown in FIGS. 4A and 4B where further dilator rotation is inhibited by indicator flange 38 abutting portion 30 of lock flange 28. Such tactile indication of unlocking is a significant advantage, particularly during use of the device in a medical procedure, where careful visual examination of the device may be highly inconvenient.

In addition to the tactile indicator, determination of whether the dilator/sheath assembly is locked or unlocked can be facilitated by a visual indicator on the device 10 such as tabs 42 and 44 as discussed above.

Dilator 14 then may be withdrawn from the sheath 12 with sheath 12 remaining in the vasculature of the patient. A catheter, guide wire or the like then can be threaded through sheath 12 (as may be assisted by lead-in section 46) and into the patient. After desired placement of the catheter, guide wire, etc., the sheath 12 is suitably removed by applying force in the directions x and x' of sheath wings 20 and 22 to axially split or shear the sheath such as along score lines 24 and 26.

The foregoing description of the invention is merely illustrative thereof, and it is understood that variations and modifications can be made without departing from the spirit or scope of the invention as set forth in the following claims.

What is claimed is:

1. An introducer device for inserting of a catheter or guide wire into a patient, the device comprising:

a a dilator and sheath, the sheath having a bore adapted to receive the dilator for insertion into a patient while circumscribed by the sheath, the dilator and sheath comprising a releasable lock that prevents relative axial movement of the dilator and sheath that circumscribes the dilator, the releasble lock engaged and disengaged by relative axial rotation of the dilator and sheath, the dilator and sheath comprising a plurality of mating surfaces to provide tactile indication to a device user of whether the dilator and sheath are locked or unlocked.

2. The device of claim 1 wherein at least one mating surface is on the dilator and at least one mating surface is on the sheath proximal end.

3. The device of claim 1 wherein the dilator mating surface abuts the sheath mating position to provide tactile indication that the dilator and sheath are in an unlocked position.

4. The device of claim 1 wherein the dilator comprises at least one protrusion that provides visual indication whether the dilator and sheath are locked or unlocked.

5. The device of claim 1 wherein the dilator comprises a hub at a proximal end of the dilator, and the dilator hub comprises at least one protrusion that provides visual indication to a user of the device whether the dilator and sheath are locked or unlocked.

6. The dilator of claim 1 wherein the dilator comprises opposing tabs outwardly extending from the dilator that provide visual indication to a user of the device whether the dilator and sheath are locked or unlocked.

7. The device of claim 6 wherein the opposing tabs extend along the dilator longitudinal axis.

8. The device of claim 6 wherein the opposing tabs are configured to aid manipulation of the device.

9. The device of claim 1 wherein the sheath proximal end contains a lead-in section that aids insertion of a catheter or guide wire through the sheath.

10. The device of claim 9 wherein the lead-in section is conically shaped.

11. The device of claim 1 wherein the dilator and sheath releasably lock by non-threaded surfaces on the dilator and sheath, the non-threaded surfaces being integral to the dilator and sheath.

12. An introducer device for inserting a catheter or guide wire into a patient, the device comprising:

a releasably locking dilator and sheath, the sheath having a bore adapted to receive the dilator for insertion into a patient while circumscribed by the sheath, the dilator comprising a hub at a proximal end of the dilator, and the dilator hub comprising a pair of outwardly protruding tabs positioned on opposing sides of the dilator hub and that provide visual indication to a user of the device of whether the dilator and sheath are locked or unlocked.

13. The device of claim 12 wherein the opposing tabs extends along the dilator hub longitudinal axis.

14. A method of introducing a catheter or guide wire into a patient comprising:

(a) providing an introducer device comprising a dilator and sheath, the sheath having a bore adapted to receive the dilator for insertion into a patient while circumscribed by the sheath, the dilator and sheath comprising 1) a releasable lock and 2) a plurality of mating surfaces on the sheath and dilator to provide tactile indication to a device user of whether the dilator and sheath are locked or unlocked;

(b) inserting the distal end of the device into a patient while the dilator and sheath are releasably locked;

(c) providing relative axial rotation between the dilator and the sheath to abut a mating surface of the dilator against a mating surface on the sheath and thereby provide tactile indication the sheath and dilator are locked or unlocked; and (d) withdrawing the dilator from the sheath and inserting a catheter or guide wire through the sheath into the patient.

15. The method of claim 14 wherein the dilator is axially rotated to provide tactile indication that the dilator and sheath are unlocked.

16. The method of claim 14 wherein the dilator is axially rotated about 90° to abut the mating surfaces of the dilator and sheath.

17. The device of claim 1 wherein the dilator and sheath releasably lock through a threaded engagement.

18. The device of claim 17 wherein the dilator hub distal end screws into the sheath hub proximal end.

19. The device of claim 1 wherein the dilator and sheath releasably lock through a luer lock engagement.

20. The device of claim 2 wherein the dilator mating surface is a flange on a dilator hub on the dilator proximal end, the dilator mating surface extending outwardly from the dilator hub.

21. The device of claim 20 wherein the dilator mating surface abuts an upstanding flange on a sheath hub on the sheath proximal end.

22. The device of claim 1 wherein the plurality of mating surfaces that provide tactile indication are integral components of the releasable dilator and sheath lock.

23. The method of claim 14 wherein the releasble lock is engaged and disengaged by relative axial rotation of the dilator and sheath.

* * * * *